United States Patent [19]
Ohlenschläger et al.

[11] Patent Number: 5,925,620
[45] Date of Patent: Jul. 20, 1999

[54] THERAPEUTICALLY ACTIVE MIXTURE OF GLUTATHIONE AND ANTHOCYANIN COMPOUNDS

[76] Inventors: Gerhard Ohlenschläger, Hauptstr. 22, 6240 Königstein, Germany; Gernot Treusch, Offenbacher Landstr. 416/418, 6000 Frankfurt am Main 70, Germany

[21] Appl. No.: 08/815,552

[22] Filed: Mar. 12, 1997

Related U.S. Application Data

[62] Continuation of application No. 08/599,115, Feb. 9, 1996, abandoned, which is a continuation of application No. 08/280,379, Jul. 26, 1994, abandoned, which is a continuation of application No. 08/158,803, Nov. 24, 1993, abandoned, which is a continuation of application No. 07/938,040, filed as application No. PCT/EP91/01580, Aug. 20, 1991, abandoned.

[30] Foreign Application Priority Data

Aug. 20, 1990 [DE] Germany ..................................... 40263

[51] Int. Cl.$^6$ .................................................. A61K 38/00
[52] U.S. Cl. ............................................. 514/18; 530/331
[58] Field of Search ................................ 514/18; 530/331

[56] References Cited

U.S. PATENT DOCUMENTS

| | | | |
|---|---|---|---|
| 2,760,956 | 8/1956 | Brick ........................................ | 260/112 |
| 3,984,569 | 10/1976 | Kalopissis et al. ...................... | 424/319 |
| 4,229,439 | 10/1980 | Majole .................................... | 424/180 |
| 4,258,055 | 3/1981 | Lietti et al. ............................. | 514/456 |
| 4,413,004 | 11/1983 | Lietti et al. ............................. | 514/456 |

FOREIGN PATENT DOCUMENTS

| | | |
|---|---|---|
| 27 40 346 | 9/1978 | Germany . |
| 3615313A1 | 11/1986 | Germany . |
| 2808823C2 | 3/1988 | Germany . |
| WO 89/00427 | 1/1989 | Germany . |
| 1444024 | 7/1976 | United Kingdom . |

OTHER PUBLICATIONS

Raynal et al., *J. Agric. Food Chem.*, 37, pages 1051–1053, 1989.

Vince and Wadd, "Glyoxalase Inhibitors as Potential Anticancer Agents," *Biochem. and Biophys. Res. Comm.*, 35(5):593 (1969).

Ohlenschläger et al., "Die Lipidperoxidation —ein für viel Erkrankungen grundlegendes pathobiochemisches Problem" (The Lipidperoxidation —a basic pathobiological problem concerning many diseases), Arztezeitschr. f. Nat. u. Reg. Sep. 1989, 30 Jhrg. Scientific Journal for Natural Medicine, pp. 713–727.

Brunmark et al., "Redox and Addition Chemistry of Quinoid Compounds and its Biological Implications," *Free Radical Biology & Medicine*, vol. 7, pp. 435–477, 1989.

Flohe et al., "Protective Function of Reduced Glutathione (G–SH) Against the Effect of Prooxidative Substances and of Irradiation in the Red Cell," *Glutathione —Proceedings of the 16th Conference of the German Society of Biological Chemistry, Tübingen*, pp. 192–199, George Thieme Publishers Stuttgart, 1974.

Larsson et al., "Functions of Glutathione Biochemical, Physiological, Toxicological, and Clinical Aspects," Raven Press, New York, 1983, pp. 51–64, 99–108, 125–137, 149–161, 163–173, 199–203, 205–213, 215–222, 231–242, 243–250, 251–260, 261–271, 297–305, and 307–315.

Ohlenschläger, "Tumorproliferation and Tumorprogression," *Therapeutikon* 10, 555–568, Oct. 1988.

Ohlenschläger, "Umweltbelastung und Krebserkrankungen" (Environmental Pollution and Cancer), *Natur–und Ganzheitsmedizin*, 4, pp. 18–21, Apr. 1991.

Ohlenschläger et al., "Die Selen–abhängigen Glutathion–Peroxidasen" (The Selenium–dependent Glutathione Peroxidase), *Natur–und GanzheitsMedizin*, 4, pp. 258–265, Apr. 1991.

Ohlenschläger et al., "Freie Radikale –aktivierte Sauerstoff–Stufen und das Phänomen der Lipidperoxidation" (Free Radicals —Activated Oxygen–Levels and the Phenomenon of Lipid Peroxidation), *Natur–und Ganzheits-Medizin*, 3, pp. 381–391, Mar. 1990.

Ohlenschläger et al., "Wie frei sind „freie" Radikale in lebenden Systemen?" (How Free are "Free" Radicals in Living System?), *Erfahrungsheilkunde*, pp. 55–70, Feb., 1988

Smith, "Correlations and Apparent Contradictions in Assessment of Oxidant Stress Status in Vivo," *Free Radical Biology & Medicine*, vol. 10, pp. 217–224, 1991.

Mannervik et al., "The Catalytic Mechanism of Glutathione Reductase," *Flavins and Flavoproteins*, Bd. 6, 1980, pp. 173–188.

A.M. Novi, "Regression of Aflatoxin $B_1$–Induced Hepatocellular Carcinomas by Reduced Glutathione," *Science*, vol. 212 (4494):541 (May, 1981).

J.P. Perchellet et al., "Effects of Combined Treatments with Selenium, Glutathione, and Vitamin E on Glutathione Peroxidase Activity, Ornithine Decarboxylase Induction, and Complete Multistage Carcinogenesis in Mouse Skin," *Cancer Research*, 47(2):477, Jan. 15, 1987.

M.E. Anderson et al., "Glutathione Monoethyl Ester: Preparation, Uptake by Tissues, and Conversion to Glutathione," *Arch. of Biochemistry and Biophysics*, vol. 239(2):538 (Jun., 1985).

(List continued on next page.)

*Primary Examiner*—Cecilia J. Tsang
*Assistant Examiner*—C. Delacroix-Muirheid
*Attorney, Agent, or Firm*—Alston & Bird LLP

[57] ABSTRACT

A mixture of substances for therapeutically treating the human or animal body contains reduced glutathion and at least an anthocyan compound from the group composed of pelargonidine, peonidine, cyanidine, melvidine, petunidine and delphinidine. The reduced glutathion can be entirely or partially substituted by at least a thiol-derivate of glutathion from the group composed of methyl-glutathionyl-(thio)-ether, ethylglutathionyl-(thio)-ether, mono-acetyl-glutathionyl-(thio)-ester and mono-phosphoric acid glutationyl-(thio)-ester.

36 Claims, No Drawings

OTHER PUBLICATIONS

E. Beutler et al., "Plasma Glutathione in Health and in Patients with Malignant Disease," *J. Lab. Clin. Med.*, 105:581 (May, 1985).

Kühnau, "The Flavonoids. A Class of Semi–Essential Food Components: Their Role in Human Nutrition," *Wld Rev. Nutr. diet.*, vol. 24, pp. 117–191 (1976).

Hagen et al., "Bioavailability of dietary glutathione: effect on plasma concentration," *Amer. Physiological Society*, pp. 524–529, 1990.

Maellaro et al., "Lipid peroxidation and antioxidant systems in the liver injury produced by glutathione depleting agents," *Biochem Pharmacol*, 39(10):1513–1521 (May 15, 1990) (Abstract only).

Bland et al., *medical Applications of Clinical Nutrition*, pp. 46–47 (1983).

"Vitamin A, Beta–Carotene and other Carotenoids," *Vitamin A & Carotenoids*, Textbook of Natural Medicine, vol. 1, 1986, pp. 1–11.

Reed, et al., "Glutathione Depletion and Susceptibility," *Pharmacological Reviews*, pp.25S–33S, 1984.

Werbach, *Nutritional Influences on Illness*, pp. 120, 140–141, 158, 201.

Minkova et al., "Antiradiation Properties of Alpha Tocopherol, Anthocyans, and Pyracetam Administered Combined as a Pretreatment Course," *Bulgarian Academy of Sciences*, pp. 31–35, 1990.

"Guarding Against Cellular Glutathione Deficiency," *Nutrition Reviews*, vol. 48, No. 9, pp. 346–348, Sep., 1990.

Di Re et al., "Efficacy and safety of high–dose cisplatin and cyclophosphamide with glutathione protection in the treatment of bulky advanced epithelial ovarian cancer," *Cancer Chemother Pharmacol*, 25:355–360 (1990).

Nobile et al., "A Preliminary Clinical Study of Cyclophosphamide with Reduced Glutathione as Uroprotector," *Tumori*, 75:257–258 (1989).

Cutler, "Antioxidants and Aging," *Am. J. Clin. Nutr.*, 53:373–379 (1991).

Corbucci et al., "Shock–Induced Damage to Mitochondrial Function and Some Cellular Antioxidant Mechanisms in Humans," *Circulatory Shock*, 15:15–26 (1985).

Keller et al., "Decreased Hepatic Glutathione Levels in Septic Shock," *Arch Surg*, vol. 120, pp.941–945 (Aug., 1985).

Shi et al., "Factors influencing hepatic glutathione concentrations: a study in surgical patients," *Clinical Science*, 62:279–283 (1982).

Ferrari et al., "Role of oxygen free radicals in ischemic and reperfused myocardium," *Am J Clin Nutr*, 53:215–222 (1991).

Tedeschi et al., "The role of glutathione in combination with cisplatin in the treatment of ovarian cancer," *Cancer Treatment Reviews*, 18:253–259 (1991).

Lash et al., "Exogenous glutathione protects intestinal epithelial cells from oxidative injury," *Proc. Natl. Acad. Sci.*, vol. 83, pp.4641–4645, (Jul., 1986).

Meister, "Selective Modification of Glutathione Metabolism," *Science*, vol. 220, pp. 472–477 (Apr., 1983).

Vincenzini et al., "Glutathione–mediated transport across intestinal brush–border membranes," *Biochimica et biophysica Acia*, 942:107–114 (1988).

Braverman et al., "The Healing Nutrients Within —Facts, Findings and new Research on Amino Acids," p.93 (1987).

J. Molnar, et al.; Antitumor Activity of Flavonoids on NK/Ly Ascites Tumor Cells; Neoplasma, 28, 1, 1981, pp. 11–18.

Pharmacological Research Communications, vol. 18, No. 1, 1986, pp. 61–72.

Mou–Tuan Huang, et al.; Inhibition of the mutagenicity of bay–region diol–epoxides of polycyclic aromatic hydrocarbons by phenolic plant flavonoids; Carcinogenesis vol. 4 No. 12, pp. 1631–1637, 1983.

Chemical Abstracts, vol. 105, 1986, Ref. 120591b.

Chemical Abstracts, vol. 108, 1988, Ref. 11248m.

THERAPEUTICALLY ACTIVE MIXTURE OF GLUTATHIONE AND ANTHOCYANIN COMPOUNDS

This application is a continuation of application Ser. No. 08/599,115, filed Feb. 9, 1996, now abandoned, which is a continuation of application Ser. No. 08/280,379, filed Jul. 26, 1994, now abandoned, which is a continuation of application Ser. No. 08/158,803 filed Nov. 24, 1993, now abandoned, which is a continuation of application Ser. No. 07/938,040, filed Nov. 12, 1992 which is now abandoned, which is a national stage of PCT/EP91/01580, filed on Aug. 20, 1991.

Scientific findings of the past few years show that destructive physical chemical processes by "free" radicals, radical chain reactions, and/or activated oxygen states become ever more important aspects in the pathogenesis of many acute diseases and especially of chronic diseases, among others of arterial and venous angiopathies, allergies, autoaggressive diseases, and tumors. Reactions of "free" radicals and activated oxygen states (ASS) and also of radicals formed by ionizing radiation in water radiolysis always lead to changes and destructions of the biomolecules (DNA, RNA, enzyme and structural proteins, unsaturated fatty acids, etc.) and also to membrane damage and membrane destruction in all cells and cell organellae by way of radical reaction phenomena of the lipoperoxidation. Radical processes are included in the etiology of all diseases; often they even are the cause of these diseases, or they sustain them by radical chain reactions.

For this reason man and animals are protected by certain enzymes having anti-oxidative action, such as superoxide dismutases, catalases, and peroxidases which "defuse" the activated oxygen states.

It is known (WO 89/00427) that the reduction potential of reduced glutathione, i.e. its optimum high intracellular concentration, is extremely important to maintain the functioning of many, perhaps all the enzymes of cell metabolism, to prevent oxidative alterations of their catalytic and allosteric centers, and to uphold optimum conformation, and that it can be increased by doses of reduced glutathione or at least be reestablished—where the metabolism dysfunctions.

It is likewise known (WO 89/00427) that it may be more favorable to supply a thiol derivative of glutathione to the body from outside, instead of the reduced glutathione itself Thiol derivatives are characterized by a particularly good bioavailability. Their capability of permeation through biological membranes is high. The SH group of glutathione which is important for the therapeutic effect is protected on the way through biological compartments up to the desired site of action, and they cause no inhibition of the enzymes which take part in the endogenous glutathione biosynthesis Likewise known (DE-OS 27 40 346) are medicines which contain an anthocyanidin, such as cyanidin, peonidin, delphinidin, petunidin, pelargonidin, and/or malvidin as the active component. These medicines are intended for use in the treatment of wounds, ulcers, inflammatory symptoms, and pathogenic conditions of the vascular system or of disturbances caused by a deterioration of the lipoid or glycide metabolisms.

Although, as a coenzyme (selenium dependent glutathione peroxidases) and as a cofactor (glutathione S transferases), but also as a non-enzymatic scavenger and nucleophilic substance, reduced glutathione can detoxify electrophilic xenobiotics directly as primary or secondary radicals and can detoxify radicals which are formed in the cell metabolism by exposition to energy-rich radiation, insufficiencies may result if reduced glutathione is the only therapy applied, even if applied sufficiently Such insufficiencies are explained by:

poor genetic equipment with anti-oxidative, i.e. scavenge enzymes (enzymopathies)

deficient biosynthesis of anti-oxidative enzymes in different compartments and in dependence on certain unfavorable phases in life (enzymopenias);

"oxidative wear" of reduced glutathione under certain circumstances, such as intoxications, inflammations, infections, shortages of non-enzymatic or enzymatic scavengers, with the extremely unfavorable possibility of the formation of thyil radicals, glutathione disulfide anionic radicals, or glutathione peroxisulphenyl radicals;

de novo biosynthesis dysfunctions of endogenous reduced glutathione;

high-performance sports, cachexies, consumptive diseases, age.

All these insufficiencies of various origin lead to alterations of the negative redox potential which exists in all biological spaces of living systems and to enzyme disorders by way of "derailing" in the "redox shifting system"

reduced glutathione ⇌ mixed disulfides ⇌ oxidized glutathione, especially so in anti-oxidative enzymes and repair enzymes, further to metabolic dysfunction, mutations, malignant transformation, or even cellular necrosis.

Now it has been found that the therapeutic failures which result from the pathogenic disorders mentioned upon exclusive use of reduced glutathione can be prevented by a combination of reduced glutathione with anthocyanins, with the possibility of advantageously using thiol derivatives of glutathione instead of the reduced glutathione or in addition to the same.

The invention thus provides a mixture of substances for therapeutic treatment of the human or animal body, which mixture contains reduced glutathione and at least one anthocyanin compound of the group consisting of pelargonidin, peonidin, cyanidin, melvidin, petunidin, delphinidin, with the reduced glutathione possibly being substituted altogether or in part by at least one thiol derivative of glutathione of the group consisting of methylglutathionyl(thio)ether, ethylglutathionyl(thio)ether, mono-acetylglutathionyl(thio) ester, mono-phosphoric glutathionyl(thio)ester.

Reduced glutathione is a tripeptide present, in its reduced form (G-SH), in most human and mammal cells; it consists of the three amino acids glutamic acid, cysteine, and glycine and has the structural formula below:

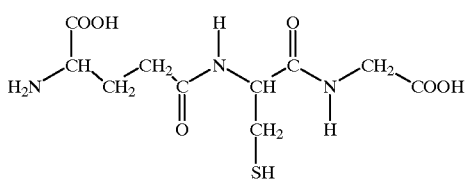

reduced glutathione (gamma-glutamyl-cysteinyl-glycine).

The thiol derivatives of glutathione used according to the invention have the following structural formula

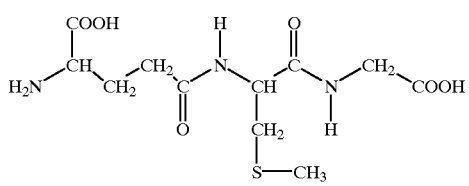

methylglutathionyl(thio)ether or monomethyl thioester

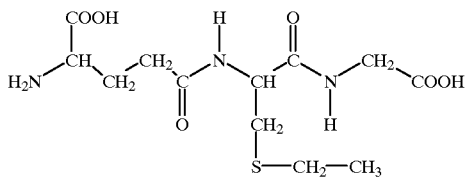

ethylglutathionyl(thio)ether or monoethyl thioester

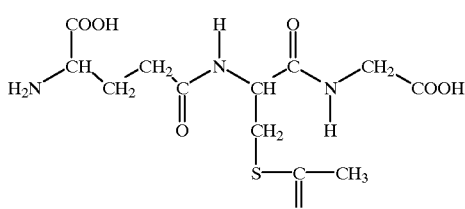

mono-acetylglutathionyl(thio)ester or monoacetyl thioester

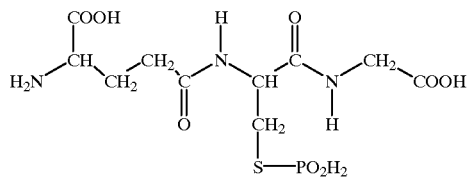

mono-phosphoric glutathionyl(thio)ester or monophosphoric thioester.

Anthocyanins are present in many plants of higher order where they are responsible for the red, violet, blue or bluish black colors of flowers and fruits They are heterocyclic 2-phenyl-chromenol multiring systems of varying hydroxylating patterns and varying absorption spectra in the visible light range. The sugar-free aglycon components of anthocyanins are referred to as anthocyanidins. They are obtained easily by hydrolysis of the glycosides contained in common fruits (cf. DE-OS 27 40 346) and their structural formula is as follows:

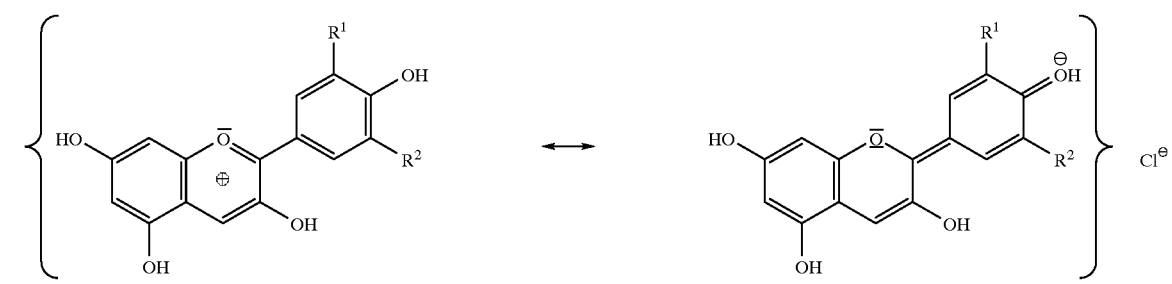

| $R^1$ | $R^2$ | popular name | $\lambda_{max}$ (nm) (color) |
|---|---|---|---|
| H | H | pelargonidin | 520 (red orange) |
| H | $OCH_3$ | peonidin | 532 (red violet) |
| H | OH | cyanidin | 535 (red violet) |
| $OCH_3$ | $OCH_3$ | malvidin | 542 (violet red) |
| OH | $OCH_3$ | petunidin | 543 (violet red) |
| OH | OH | delphinidin | 544 (blue violet) |

Anthocyanins can act as good scavengers for the superoxide anion radical ($O_2^-$), for hydrogen peroxide ($H_2O_2$), for the hydroxyl radical (OH.), for alkoxyl radicals (LO.), peroxyl radicals (L O O.), for singulett oxygen ($O_2(^1g)$), and many other radicals Anthocyanins also can act as photobiological inhibitors, intervening as regulators and detoxifiers in sensitized photoreactions which take place through oxygen, thereby preventing the radical and radical chain reactions which damage cells and molecules, regardless of how they came to be.

Anthocyanins protect against cell toxic and cancerogenic aldehydes (4-hydroxy-hexenal, 4-hydroxy-octenal, 4-hydroxy-nonenal, propanal, butanal, pentanal, hexanal, 2,4-hepta-dienal, malonic dialdehyde, and others). They even prevent the formation thereof within the framework of lipoperoxidative chain reactions Furthermore, they detoxify the acetaldehyde resulting from ethanol decomposition and the formaldehyde resulting from methanol decomposition or incorporated in other manners.

When used therapeutically, the anthocyanin compounds and reduced glutathione and/or its thiol derivatives supplement each other in optimum fashion, in response to the doses, with many cell disorders and many cell and enzyme dysfunctions. Apart from the qualitative therapeutic aspect, the combined use of reduced glutathione and/or its thiol derivatives together with anthocyanin compounds above all provides a much more effective quantum yield as regards the scavenge function. Thyil radicals (GS.), glutathione disulfide anion radicals (G-S-S-G.), and also glutathione peroxysulphenyl radicals (G-S O O.) either are prevented from forming or are detoxicated.

Moreover, not only reduction of oxidized glutathione (G-S-S-G) takes place and glutathion radicals are prevented and/or detoxified but also a sustained regeneration of the radical-detoxifying functions occurs in an oscillating reaction cycle between the two substances or groups of substances (glutathione and anthocyanins). The mutual complementation of the two groups of substances in the mixture of substances according to the invention is of such optimum nature that the reduced glutathione once again can fulfill its vital control functions to the full extent both on the genetic level and on the enzyme level and, finally, on all levels.

Reduced glutathione (G-SH) among others reacts with quinones, forming glutathionyl hydroquinone conjugates which can auto-oxidize to form the corresponding hydroquinones. The G-SH conjugate reduces the radical electrophilic character of quinones, while improving their hydrophylic nature Such formations of conjugates which are of great toxicologic interest are limited intracellularly both by the quinone concentration and that of G-SH. That presents another therapeutic approach for many diseases appearing so differently in phenomenology. Apart from the readjustment of a physiological control behavior on all biological levels and in all compartments of living systems, the combination of reduced glutathione or its thiol derivatives with anthocyanin compounds also displays therapeutic effect, above all, with radical and radical chain reactions initiated in different manner (thermally, chemically, mechanically, infectious-toxically, due to radiation, and otherwise) and with the pathobiochemically important phenomenon of lipid peroxidation.

The mixture of substances according to the invention largely prevents the cross linking of biomolecules (connective tissue, proteins, DNA, and others) with diabetes mellitus and especially also with the diabetic late syndrom (prevention of Amadori bodies). It further prevents polyneuropathic degenerations of the peripheral and central nervous systems, of lipoperoxidative origin or pathogenetic cause, in the sense of preventing the formation of lipofuscin or lipofuscin foci. Moreover, the very combination of glutathione and anthocyanin compounds makes sure that protein denaturing at bradytrophic tissues does not take place, such as at the cornea, crystalline lens, and vitreous body of the eye.

A further increase in effectiveness results from the addition of vitamin E (alpha tocopherol acetate) and/or vitamin A and/or β-carotene and/or selenium and/or L-cystein to the mixture of substances according to the invention.

Especially well suited is an oral form of administration of the mixture of substances according to the invention, the therapeutic dose ranging from 50 mg to 2400 mg per day.

The mixture of substances according to the invention thus has a corresponding wide field of pharmacological and therapeutic application. Its use is indicated, among others, for the treatment of cancerous diseases of any genesis, including malignant diseases of blood cells and their precursors, for substitution and regulation of metabolic processes when other tumor therapies are applied, such as radiation therapy and/or naturopathic therapies, for preventive treatment and therapy of metastases within the framework of malignant cancerous diseases, for treatment of hepatopathies, especially acute and chronic illness from hepatitis, such as chemical-toxic and infectious-toxic hepatitis, viral hepatitis, hepatitides caused by Rickettsiae, bacteria, or protozoa, as well as chronic aggressive hepatitis, fatty degeneration of the liver, fatty cirrhosis, and liver cirrhoses of any genesis, for the treatment of any dysfunction in the immunologic defense in the field of natural killer cells, monocytes, macrophages, granulocytes, T- and B-lymphocytes, plasma cells, and disorders of the complement factors and antibody synthesis, for the treatment of complex dysfunctions of the lymphocon biosynthesis in T-helper cells, macrophages, and other cells, for the treatment of cardiomyopathies of any genesis, also in combination with other therapies, any form of coronary ailment, angina pectoris, prophylaxis of myocardial infarction and emergency treatment of cardiac infarction together with other emergency medicines, for the treatment of acquired or congenital forms of skeletal muscle disorders, for the treatment of neurologic diseases of inflammatory, allergic, or degenerative genesis, for the treatment of all kinds of blood cell diseases, anemias, leukopenias, lymphopenias, and thrombocytopenias, for preventive treatment of crystalline lens damage, toxic disorders of the retina and vitreous body, as well as for cataract prophylaxis, for the treatment of all kinds of over-oxidation or of the oxidative stress, for example within the framework of applying oxygen therapies or therapies with activated oxygen states (oxygen radicals), and for protection in the application of hyperbaric oxygen therapy, oxygen multistep therapy, ozon therapies, and HOT therapies for intoxication leading to biomolecule and tissue damage in the human organism by radical chain reactions, as an accompanying therapy in radiation treatment, treatment with cytostatics, and for attenuating or preventing sickness, nausea, and others, following anesthesias, especially general anesthesias with patients suffering from lesions of the heart and liver, for intoxications with xenobiotics, especially with toxic trace elements and with heavy metals, for the treatment of proliferation disorders and differentiation disorders of epithelium, endothelium and mucosa tissues, for the treatment of pathophysiological arteriosclerosis and arteriosclerosis of different genesis, for basic treatment and adjuvant therapy of allergies, for the treatment of impotentia coeundi and impotentia generandi, as well as fertility disorders and disturbance of the copulative power of any genesis, upon premature aging, wear due to age of all tissues, including skin and skin connective tissues, and for preventive treatment in case of activities and habits in life that lead to premature aging or premature wear of organs and tissue.

We claim:

1. A composition consisting essentially of reduced glutathione and at least one anthocyanin compound.

2. The composition of claim 1, wherein said at least one anthocyanin compound is selected from the group consisting of pelargonidin, peonidin, cyanidin, malvidin, petunidin, and delphinidin.

3. A composition comprising at least one thiol derivative of glutathione and at least one anthocyanin compound for the therapeutic treatment of a subject.

4. The composition of claim 3, wherein said at least one thiol derivative of glutathione is selected from the group consisting of methylglutathionyl(thio)ether, ethylglutathionyl(thio)ether, mono-acetylglutathional(thio) ester, and mono-phosphoric glutathional(thio)ester.

5. The composition of claim 3, wherein said at least one anthocyanin compound is selected from the group consisting of pelargonidin, peonidin, cyanidin, malvidin, petunidin, and delphinidin.

6. The composition of claim 3, wherein said at least one anthocyanin is an anthocyanidin.

7. The composition of claim 3, further comprising at least one compound selected from the consisting of vitamin E, vitamin A, and mixtures thereof.

8. The composition of claim 3, further comprising beta-carotene.

9. The composition of claim 3, further comprising selenium.

10. The composition of claim 3, further comprising L-cysteine.

11. A composition comprising mono-acetylglutathional (thio)ester and at least one anthocyanin compound.

12. A method for increasing or maintaining intracellular concentration of glutathione in a subject, comprising concurrently administering to said subject reduced glutathione and at least one anthocyanin compound in an amount effective to increase or maintain the intracellular concentration of glutathione.

13. The method of claim 12, wherein said administering step further comprises administering at least one thiol derivative of glutathione.

14. The method of claim 13, wherein said at least one thiol derivative of glutathione is selected from the group consisting of methylglutathionyl(thio)ether, ethylglutathionyl(thio) ether, mono-acetylglutathional(thio)ester and mono-phosphoric glutathional(thio)ester.

15. The method of claim 12, wherein said at least one anthocyanin compound is selected from the group consisting of pelargonidin, peonidin, cyanidin, malvidin, petunidin, and delphinidin.

16. The method of claim 12, wherein said at least one anthocyanin compound is an anthocyanidin.

17. The method of claim 12, wherein said administering step further comprises administering at least one compound selected from the group consisting of vitamin E, vitamin A, and mixtures thereof.

18. The method of claim 12, wherein said administering step further comprises administering beta-carotene.

19. The method of claim 12, wherein said administering step further comprises administering selenium.

20. The method of claim 12, wherein said administering step further comprises administering L-cysteine.

21. A method for increasing or maintaining intracellular concentration of glutathione in a subject, comprising concurrently administering to said subject at least one thiol derivative of glutathione and at least one anthocyanin compound in an amount effective to increase or maintain the intracellular concentration of glutathione.

22. The method of claim 21, wherein said at least one thiol derivative of glutathione is selected from the group consisting of methylglutathionyl(thio)ether, ethylglutathionyl(thio) ether, mono-acetylglutathional(thio)ester and mono-phosphoric glutathional(thio)ester.

23. The method of claim 21, wherein said at least one anthocyanin compound is selected from the group consisting of pelargonidin, peonidin, cyanidin, malvidin, petunidin, and delphinidin.

24. The method of claim 21, wherein said at least one anthocyanin compound is an anthocyanidin.

25. The method of claim 21, wherein said administering step further comprises administering at least one compound selected from the group consisting of vitamin E, vitamin A, and mixtures thereof.

26. The method of claim 21, wherein said administering step further comprises administering beta-carotene.

27. The method of claim 21, wherein said administering step further comprises administering selenium.

28. The method of claim 21, wherein said administering step further comprises administering L-cysteine.

29. A method for increasing or maintaining intracellular concentration of glutathione in a subject, comprising concurrently administering to said subject mono-acetylglutathional(thio)ester and at least one anthocyanin compound in an amount effective to increase or maintain the intracellular concentration of glutathione.

30. A composition comprising reduced glutathione, at least one thiol derivative of glutathione and at least one anthocyanin compound.

31. The composition of claim 30, wherein said at least one thiol derivative of glutathione is selected from the group consisting of methylglutathionyl(thio)ether, ethylglutathionyl(thio)ether, mono-acetylglutathional(thio) ester, and mono-phosphoric glutathional(thio)ester.

32. A composition comprising reduced glutathione and at least one anthocyanidin.

33. A composition comprising reduced glutathione, at least one anthocyanin compound and a compound selected from the group consisting of vitamin E, vitamin A, and mixtures thereof.

34. A composition comprising reduced glutathione, at least one anthocyanin compound and beta-carotene.

35. A composition comprising reduced glutathione, at least one anthocyanin compound and selenium.

36. A composition comprising reduced glutathione, at least one anthocyanin compound and L-cysteine.

* * * * *